US006280726B1

(12) United States Patent
Weinrauch et al.

(10) Patent No.: US 6,280,726 B1
(45) Date of Patent: Aug. 28, 2001

(54) TYPE II PHOSPHOLIPASE A2 AND ITS USE IN KILLING GRAM-POSITIVE BACTERIA

(75) Inventors: Yvette Weinrauch; Peter Elsbach, both of New York, NY (US); Jerrold Weiss, Coralville, IA (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/232,782

(22) Filed: Jan. 19, 1999

Related U.S. Application Data

(63) Continuation of application No. 08/694,391, filed on Jul. 19, 1996, now Pat. No. 5,874,079.
(60) Provisional application No. 60/002,772, filed on Jul. 21, 1995, and provisional application No. 60/011,659, filed on Feb. 14, 1996.

(51) Int. Cl.$^7$ ..................................................... C12N 9/20
(52) U.S. Cl. ........................................... 424/94.6; 435/198
(58) Field of Search ............................. 424/94.6; 435/198

(56) References Cited

U.S. PATENT DOCUMENTS

| | | |
|---|---|---|
| 4,209,508 | 6/1980 | Mitsui et al. . |
| 4,503,040 | 3/1985 | Barth . |
| 4,882,608 | 11/1989 | Benton et al. . |
| 4,883,673 | 11/1989 | Gonzalez . |
| 4,929,445 | 5/1990 | Vandenbergh et al. . |
| 5,019,508 | 5/1991 | Johnson et al. . |
| 5,116,615 | 5/1992 | Gokcen et al. . |
| 5,338,682 | 8/1994 | Sasaki et al. . |
| 5,338,724 | 8/1994 | Gabay et al. . |
| 5,447,914 | 9/1995 | Travis et al. . |
| 5,482,723 | 1/1996 | Sasaki et al. . |
| 5,504,082 | 4/1996 | Kawakita et al. . |

OTHER PUBLICATIONS

M. Inada et al., Determinants of the Inhibitory Action of Purified 14–kDA Phospholipases $A_2$ on Cell–Free Prothrombinase Complex, J. Bio. Chem., 269:26338–343 (1994).

J. Sheagren, *Staphylococcus Aureus*, The Persistent Pathogen, New England J. of Medicine, 310:1368–69 (1994).

M. Cohen, *Antimicrobial Resistance: Prognosis for Public Health*, Trends in Microbiol. 2:422–425 (1994).

G. Wright et al., Purification of a Cellular (Granulocyte) and an Extracellular (Serum) Phospholipase $A_2$ that Participate in the Destruction of *Escherichia coli* in a Rabbit Inflammatory Exudate, J. of Biol. Chem., 265:6675–6681 (1990).

Weiss et al., Structural Determinants of the Action Against *Escherichia coli* of a Human Inflammatory Fluid Phospholipase $A_2$, J. of Bio. Chem., 269:26331–337 (1994).

J. Bomalaski et al., Human Extracellular Recombinant Phospholipase $A_2$ Induces an Inflammatory Response in Rabbit Joints, J. of Immuno., 146:3904–910 (1991).

G. Cirino et al., Recombinant Secreted Nonpancreatic Phospholipase $A_2$ Induces a Synovitis–Like Inflammation in the Rat Air Pouch, J. of Reuma., 21:824–29 (1994).

A. Santos et al., Are Events after Endotoxemia Related to Circulating Phospholipase $A_2$?, Annals of Surgery, 219:183–192, (1994).

D. Snyder et al., Characterization of the Contractile effects of Human Recombinant Nonpancreatic Secretory Phospholipase $A_2$ (PLA$_2$) and Other PLA$_2$s on Guinea Pig Lung Pleural Strips, J. of Pharmac. and Exp. Thera., 266:1147–55 (1993).

M. MacPhee et al., The Secretory Phospholipase $A_2$ Gene is a Candidate for the Mom1 Locus, and Major Modifier of Apc$^{Min}$–Induced Intestinal Neoplasia, Cell 81:957–966 (1995).

R. Kramer, Structure and Properties of a Human Non–pancreatic Phospholipase $A_2$, J. of Bio. Chem., 264:5768–775 (1989).

Weinrauch et al., Extracellular Accumulation of Potently Microbicidal Bactericidal/Permeability–Increasing Protein and p15s in an Evolving Sterile Rabbit Peritoneal Inflammatory Exudate, J. Clin. Invest., 95:1916–1924 (1995).

E. Dennis, Diversity of Group Types, Regulation, and Function of Phospholipase $A_2$, J. Biol. Chem., 269:10357–360 (1994).

S. Harwig et al., Bactericidal Properties of Murine Intestinal Phospholipase $A_2$, J. Clin. Invest., 95:603–610 (1995).

S. Reddy et al.,Analysis of the Secretory Phospholipse $A_2$ that Mediates Prostaglandin Production in Mast Cells, J.of Bio. Chem., 272:13591–596.

*Primary Examiner*—Leon B. Lankford, Jr.
(74) *Attorney, Agent, or Firm*—Darby & Darby

(57) ABSTRACT

Disclosed herein are methods for killing Gram-positive bacterial infections in animals comprising exposing the bacteria to Gram-positive bactericidal-effective amounts of Type II phospholipase A2. The Type II phospholipase A2 can be isolated from mammalian species including humans, cows, rabbits, rats, mice, cats, and dogs. Type II phospholipase A2 is effective in treating infections in mammals, including humans, caused by gram-positive bacteria such as *Staphylococcus aureus*. Also disclosed are pharmaceutical formulations for use in the methods.

7 Claims, 5 Drawing Sheets

TYPE II PHOSPHOLIPASE A2 AND ITS USE IN KILLING GRAM-POSITIVE BACTERIA

This is a continuation, of application Ser. No. 08/694,391, filed Jul. 19, 1996 now U.S. Pat. No. 5,874,079. Each of these prior applications is hereby incorporated herein by reference, in its entirety.

This Application claims the benefit of U.S. provisional application No. 60/002,772, filed Jul. 21, 1995, and U.S. provisional application No. 60/011,659, filed Feb. 14, 1996

FIELD OF INVENTION

This invention pertains to methods and compositions for killing Gram-positive bacteria, such as, for example, bacteria of the generi Staphyl Streptococcus, and Bacillus, using as a bactericidal agent Type II phospholipase A2 (PLA2(II)).

BACKGROUND OF THE INVENTION

Gram-positive bacterial infections are widespread and represent a significant proportion of iatrogenic and other infections prevalent in hospitals and medical facilities. The inevitable development of antibiotic-resistant strains necessitates the continuous development of new means of controlling these infections. Thus, there is a need in the art for methods and compositions useful in treating Gram-positive bacterial infections in animals and humans (Waldvogel, in *Principles and Practice of Infectious Diseases*, Mandell et al.,eds., John Wiley, New York, 1995, pp 1754–1775).

In mammals, inflammation is a complex response that involves, at a minimum, the recruitment of immune cells, changes in vascular permeability, and the accumulation of extracellular fluid containing a wide variety of bioactive compounds, including proteins and peptides. Among the bioactivities expressed in such inflammatory fluids are antibacterial activities that are directed against both Gram-positive and Gram-negative bacteria.

In rabbits, sterile injection of glycogen into the peritoneal cavity induces the formation of a cell-rich exudate consisting of polymorphonuclear leukocytes (PMNs) and a cell-free (ascitic) fluid (designated AF). In this model system, potent antibacterial activity accumulates in AF against both Gram-negative and Gram-positive bacteria. The activity against Gram-negative bacteria is attributable to two PMN-derived antibacterial proteins acting synergistically, the Bactericidal/Permeability-Increasing Protein (BPI) and the p15s (Weinrauch et al., *J. Clin.Invest.* 95:1916, 1995). The Gram-negative bactericidal activity of AF is abolished by anti-BPI serum, indicating an absolute dependence on BPI. Antibacterial activity in AF against Staphylococci, by contrast, is unaffected by anti-BPI serum, indicating that BPI is not responsible for Gram-positive killing.

The present inventors have unexpectedly discovered that the Gram-positive bactericidal activity of rabbit AF is due to Type II phospholipase A2 (PLA$_2$(II)) that is present in the exudate. The bactericidal activity of PLA$_2$(II) is independent of other constituents and is specific to Gram-positive bacterial targets. Furthermore, Gram-positive bactericidal activity has been found to be a property of all tested members of the PLA$_2$(II) enzyme family, such as those derived from other tissues and mammalian species. Prior to the present invention, no independent bactericidal activity expressed in biological fluids (including unmodified plasma and inflammatory fluids) was ascribed to this protein. The present invention thus provides methods and compositions for killing Gram-positive bacteria that are applicable to many different therapeutic applications and that provide an important therapeutic modality to treat antibiotic-sensitive and antibiotic-resistant Gram-positive bacterial infections.

SUMMARY OF THE INVENTION

The present invention encompasses methods for killing Gram-positive bacteria, which are carried out by exposing the bacteria to a bactericidal-effective amount of Type II phospholipase A2 (PLA$_2$(II)). The PLA2(II) may be derived from mammalian species such as human, cow, rabbit, rat, mouse, dog, cat and the like, and may be isolated from a native or recombinant source. Typically, a bactericidal-effective amount of PLA$_2$(II) will range from about 0.05 to about 100 ng/ml, depending upon the bacterial species and source of PLA$_2$(II).

In another aspect, the present invention provides methods for treating Gram-positive bacterial infections in animals, including humans, by administering bactericidal-effective amounts of PLA$_2$(II).

In yet another aspect, the invention provides pharmaceutical formulations having bactericidal activity against Gram-positive bacteria. These formulations comprise bactericidal-effective concentrations of PLA$_2$(II) and a pharmaceutically acceptable carrier or diluent. Additionally, the formulations may comprise other bioactive compounds, such as, e.g., conventional antibiotics, that act additively or synergistically with PLA$_2$(II) to promote bacterial killing.

DETAILED DESCRIPTION OF THE INVENTION

Figure 1:
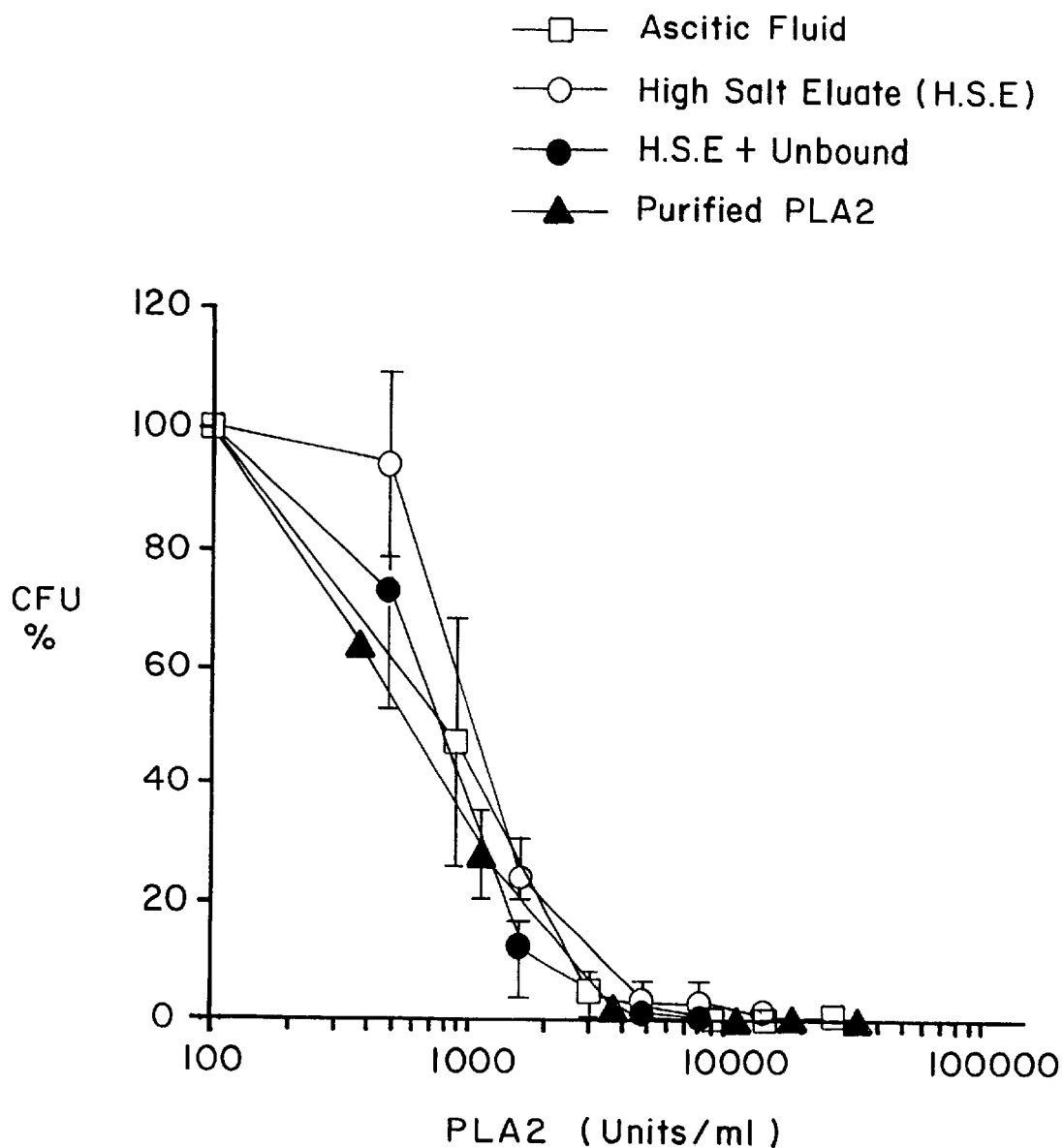
FIG. 1 is a graphic illustration of the relationship between PLA$_2$(II) enzymatic activity (X-axis) and bactericidal activity against *Staphylococcus aureus* (Y-axis) of whole rabbit ascites fluid (AF), partially purified PLA$_2$(II), and purified PLA$_2$(II).

All patent applications, patents, and literature references cited in this specification are hereby incorporated by reference in their entirety. In case of inconsistencies, the present description, including definitions, will control.

The present invention is directed to methods and compositions for killing Gram-positive bacteria that take advantage of the Gram-positive bactericidal action of Type II phospholipase A2 (PLA$_2$(II)). In practicing the invention, bacteria are exposed to, or contacted with, a Gram-positive bactericidal-effective amount of PLA2(II), resulting in the rapid inactivation and death of Gram-positive bacteria. According to the invention, bacterial infections in animals, including humans, can be treated by administering PLA$_2$(II). The invention also encompasses pharmaceutical formulations suitable for therapeutic administration.

PLA$_2$(II) as used herein refers to a subcategory of the family of low-molecular-weight phospholipase A2 enzymes, which are low-molecular weight phospholipases that hydrolyze the sn-2 fatty acyl ester bond of phosphoglycerides to produce free fatty acids and lysophospholipids (Dennis, *J.Biol. Chem.* 269:13057, 1994). Typically, PLA$_2$(II)s are characterized by the presence of a half-cystine at residue 50 and a carboxyterminal extension containing a half-cystine residue, and by the absence of half-cystines at residues 11 and 77 (which are characteristic of Type I PLA-2s). PLA$_2$(II)s for use in the present invention may be derived from any mammalian species, including without limitation human, monkey, cow, rabbit, rat, mouse, dog, and the like. The only requirement is that the PLA$_2$(II) polypeptide exhibit specific independent bactericidal activity against Gram-positive bacteria. This antibacterial activity of PLA$_2$(II) may be measured using any procedure well-known in the art, including that described in Example 2 below.

PLA$_2$(II) may be obtained from native or recombinant sources. PLA2(II) has been isolated from a wide variety of tissues derived from different mammalian species (Dennis, *J.Biol. Chem.* 269:13057, 1994). Native sources include without limitation naturally or artificially induced inflammatory fluids such as ascites, which are produced in a mammal in response to inflammatory stimuli such as glycogen, air, casein, and lipopolysaccharides. Other native sources include serum (rabbit), platelets (rabbit, rat), polymorphonuclear leukocytes, and Paneth cells.

Recombinant PLA$_2$(II) may be produced by transformation of PLA$_2$(II)-encoding DNA into any appropriate host cell, including without limitation bacterial, yeast, insect, and mammalian cells. In a preferred embodiment, CHO-K1 cells (ATCC CCL61) stably transformed with a cDNA encoding human PLA$_2$(II) are used as a source of PLA$_2$(II) (as described in Weiss et al., *J.Biol. Chem.* 269:26331, 1994). Methods for recombinant DNA manipulations and cell transformation are well-known in the art. Using methods such as those in, for example, Maniatis, *Molecular Cloning* (Cold Spring Harbor Laboratories, 1988), PLA$_2$(11)-encoding cDNAs from any mammalian species can be obtained using oligonucleotide probes of pre-determined sequence that are based on the known DNA sequence of, for example, human PLA$_2$(II) (Genbank accession nos. Gb-pr:Hsu03090 and Gb-ro:Ratpla2). For recombinant expression, PLA2(II)-encoding DNA, contained within a DNA vector, must be operably linked to a transcriptional promoter so that functional PLA$_2$(II) mRNA is transcribed and PLA$_2$(II) protein is synthesized within the transformed host cell. Preferably, PLA$_2$(II) is also secreted into the culture medium of transformed cells, which process (1) promotes formation of proper disulfide bonds necessary for PLA$_2$(II) activity and (2) facilitates purification. Alternatively, the expressed protein is subjected in vitro to reversible denaturation/reduction followed by renaturation/oxidation to promote proper disulfide bond formation.

PLA$_2$(II) DNA may also be cloned so that DNA encoding additional amino acid residues is fused in frame to the PLA$_2$(II)-encoding sequence, resulting in an expressed PLA$_2$(II) product containing additional amino acid sequences at either amino- or carboxy-terminal ends. The additional sequences may serve as, for example, purification tags that allow one-step purification of the protein after which they may be chemically or enzymatically removed. Alternatively, the additional sequences may confer an additional cell-surface binding site or otherwise alter the target cell specificity of PLA$_2$(II) (see below).

Purification of PLA$_2$(II) from natural or recombinant sources may be achieved by methods well-known in the art, including without limitation ion-exchange chromatography, reverse-phase chromatography on C4 columns, gel filtration, isoelectric focusing, affinity chromatography, immunoaffinity chromatography, and the like. In a preferred embodiment, a cell-free fluid containing PLA$_2$(II) is subjected to ion-exchange chromatography on CM-Sephadex, followed by reverse-phase high performance liquid chromatography (HPLC) on a C4 column. Purity of the final PLA$_2$(II) preparations is assessed by SDS-PAGE, amino acid sequence analysis, and laser desorption mass spectrometry. These methods are described in more detail below.

According to the present invention, PLA$_2$(II)s are characterized by both bactericidal activity against Gram-positive bacteria and by phospholipase enzymatic activity. Antibacterial activity of PLA$_2$(II) may be quantified by measuring the colony-forming ability of bacteria that have been incubated with or without increasing amounts of PLA2(II). Typically, a suspension of $10^6$ bacteria/ml (*S. aureus* or *B. subtilis*) is exposed to 0.05–100 ng/ml of PLA$_2$(II) for 30–90 minutes at 37° C., after which the cells are mixed with molten agar and plated. After overnight growth, bacterial colonies are compared between PLA$_2$(II)-treated and untreated cultures.

The LD$_{90}$ of a given preparation is defined as the concentration of PLA$_2$(II) that reduces the colony-forming potential of a bacterial culture by 1 log (i.e., kills 90% of the viable cells). A typical preparation of PLA$_2$(II) (>99% pure) assayed in this manner exhibits an LD$_{90}$ of between about 5 and about 100 ng/ml against *S. aureus*, and an LD$_{90}$ of between about 0.05 and about 2 ng/ml against *B. subtilis*. PLA$_2$(II) preparations useful in practicing the present invention will generally exhibit an LD$_{90}$ of $\leq 1$ μg/ml.

Phospholipase activity is quantified by measuring the release of soluble radiolabelled products from autoclaved [1-$^{14}$C] oleate-labelled *E. coli* (Wright et al., *J.Biol. Chem.* 265:6675, 1990). In this assay, one PLA$_2$(II) activity unit is defined as the amount of enzyme necessary to achieve 1% hydrolysis/hour, corresponding to hydrolysis of 50 pmol of phospholipid/hour. 1 unit according to this definition is equivalent to about $8.3 \times 10^{-7}$ IU (international units). Typical preparations of PLA$_2$(II) have a specific enzymatic activity of between about $1 \times 10^8$ and about $4 \times 10^8$ units/mg (corresponding to about 120 to 480 IU/mg).

PLA$_2$(II) Variants

The present invention encompasses variant forms of PLA$_2$(II) that may be formed by classical or reverse genetic manipulations and having detectable Gram-positive bactericidal activity. The methods and compositions of the present invention encompass any deletion, addition, or substitution mutant of PLA$_2$(II) that maintains at least 20% of the wild-type enzymatic and antibacterial activity. Such variants include without limitation recombinant PLA$_2$(II)s containing an additional purification tag (as described above) that is useful for immunoaffinity purification using immobilized antibodies or for affinity purification using immobilized ligands. Furthermore, useful PLA2(II) variants may contain mutations, including deletions or additions of one or more nucleotides, that either enhance or diminish homing of the enzyme to various biological targets while maintaining a cell-killing capability.

It will be understood that the methods for expression, purification, and activity measurements described above for wild-type PLA$_2$(II) can also be applied to variant PLA$_2$(II) species. Thus also, only routine experimentation is required to identify useful PLA$_2$(II) variants.

Therapeutic Applications

The methods and compositions of the present invention may be used in any clinical situation in which it is desired to kill Gram-positive bacteria in a human or other animal, including bacteremia, abscesses, surface lesions, and the like.

Gram-positive bacteria to which the methods and compositions of the present invention can be applied encompass without limitation those of the generi Micrococcus, Staphylococcus, Streptococcus, Peptococcus, Peptostreptococcus, Enterococcus, Methanobacterium, Bacillus, Clostridium, Lactobacillus, Listeria, Erysipelothrix, Corynebacterium, Propionibacterium, Eubacterium, Actinomyces, Arachnia, Bifidobacterium, Bacterionema, Rothia, Mycobacterium, Nocardia, Streptomyces, and Micropolyspora (Classification according to Joklik et al., Zinsser Microbiology, 16th Edition, Appleton, New York, 1976). Pathological conditions in humans caused by Gram-positive bacteria include, for example, pneumococcal pneumonia, local and systemic staphylococcal infections, toxic shock syndrome, osteomyelitis, scarlet fever, pyoderma, and cellulitis (Petersdorf et al., *Harrison's Principles of Internal Medicine*, 10th Edition, McGraw-Hill, 1984).

According to the present invention, native or recombinant $PLA_2(II)$ may be formulated with a physiologically acceptable carrier, such as, for example, phosphate buffered saline or deionized water. Preferably, formulations intended for use in humans will comprise human $PLA_2(II)$ or variants thereof. The pharmaceutical formulation may also contain excipients, including preservatives and stabilizers, that are well-known in the art. The compounds can be formed into dosage units such as, for example, liquids, tablets, capsules, powders, suppositories, and may additionally include excipients that act as lubricant(s), plasticizer(s), colorant(s), absorption enhancer(s), bactericide(s), and the like. The dosage forms may contain PLA2(II) at concentrations ranging from about 0.1 ng/ml to about 1000 ng/ml (for liquid or semi-liquid formulations). Solid dosage forms such as tablets and powders may contain $PLA_2(II)$ at appropriate concentration so that bactericidal effective amounts of $PLA_2(II)$ (see below) can be delivered using conventional administration regimens. It will be understood that the pharmaceutical formulations of the present invention need not in themselves contain the entire amount of the agent that is effective in treating the disorder, as such effective amounts can be reached by administration of a plurality of doses of such pharmaceutical formulations.

Modes of administration of $PLA_2(II)$ to achieve a therapeutic benefit include oral and enteral, intravenous, intramuscular, subcutaneous, transdermal, transmucosal (including rectal and buccal), and by-inhalation routes. $PLA_2(II)$s are extremely stable proteins and tolerate a wide variety of environmental conditions. It will be understood that the mode of administration will depend on the nature of the syndrome, including the location and severity of the Gram-positive bacterial infection. For example, skin lesions may be treated using a topical ointment, whereas a bacteremia may require intravenous administration. An internal but localized infection may be treated by injecting the formulation directly into the site of the infection.

An "effective amount" of $PLA_2(II)$ for treating a particular bacterial infection is an amount that results in a detectable reduction in the severity of the infection. This may be measured directly, i.e., by counting or culturing the pathogenic microorganisms, or indirectly, by monitoring clinical signs of infection, such as fever or purulent discharge. Typically, administration of $PLA_2(II)$ will result in the lessening or amelioration of at least one symptom of the infection. Any amelioration resulting from administration of $PLA_2(II)$ of any symptom of infection is within the scope of the invention. The effective amount for treating a given syndrome in a human or in other animals can be determined by routine experimentation well-known in the art, such as by establishing a matrix of dosages and frequencies and comparing a group of experimental units or subjects to each point in the matrix. Different Gram-positive bacterial species exhibit different intrinsic sensitivities to the bactericidal effects of $PLA_2(II)$ (see Example 6 below); thus, the relative dosages required for different infections may be extrapolated from the relative $LD_{90}$s of $PLA_2(II)$ for different bacteria as measured in vitro.

An additional consideration in establishing the optimum dosage of $PLA_2(II)$ for treating bacterial infections in an animal is potential toxicity. Though there have been reports that $PLA_2(II)$ possesses inflammatory activity (see, for example, Bomalaski et al., *J. Immunol.* 146:3904, 1991; and Cirino et al., *J. Rheumatol.* 21:824, 1994), this phenomenon was only observed at $PLA_2(II)$ concentrations several orders of magnitude higher than those at which bactericidal effects are observed. Furthermore, the preparations used in the studies cited above were contaminated with endotoxin, which itself has a potent inflammatory activity. Thus, without wishing to be bound by theory, it is contemplated that bactericidal effective amounts of $PLA_2(II)$ can be administered to humans and other animals without causing inflammatory or other detrimental side effects. In addition, it is preferable to treat an animal or human with $PLA_2(II)$ derived from the same species.

The amount of $PLA_2(II)$ to be administered may range from about 1 to about 1000 ng/kglday, preferably from about 10 to about 100 ng/kg/day. In a preferred embodiment, human $PLA_2(II)$ is formulated in a sterile saline solution, which is administered intravenously to a patient suffering from an antibiotic-resistant *S. aureus* bacteremia at a daily dose of from about 10 $\mu$g to about 50 $\mu$g. In another preferred embodiment, a cream containing 50 ng/ml human $PLA_2(II)$ is applied to a staphylococcal skin lesion. In a particularly preferred embodiment, a solution of 50 ng/ml human $PLA_2(II)$ is injected directly into the site of an abcess.

In another embodiment, an antibacterial formulation is prepared containing, in addition to $PLA_2(II)$, other, conventional, antibiotics (such as, for example, β-lactam antibiotics), or other bioactive substances, that may act additively or synergistically with $PLA_2(II)$ to kill Gram-positive bacteria. Without wishing to be bound by theory, it is believed that the postulated mechanism of $PLA_2(II)$-mediated Gram-positive bacterial killing (that is, disruption of the bacterial membrane) will facilitate the use of formulations containing lower doses of $PLA_2(II)$ in conjunction with, for example, sub-lethal doses of other antibiotics. This would provide a clinical advantage in reducing the overall administration of antibiotics (thus lessening the development of antibiotic-resistant strains).

Antibiotics that can be used in conjunction with $PLA_2(II)$ in the methods and compositions of the present invention include without limitation penicillins (such as ampicillin, amoxicillin, methicillin, and the like), cephalosporins, aminoglycosides (such as streptomycin, neomycin, kancmycin, gentamicin, and the like), tetracyclines, chloramphenical, and vancomycin.

The following examples are intended to further illustrate the invention without limiting its scope thereof.

EXAMPLE 1

Purification of $PLA_2(II)$ from Rabbit Ascitic Fluid (1) Collection of ascitic fluid (AF) Sterile inflammatory peritoneal exudates were elicited in New Zealand White rabbits (2–3 kg) by intraperitoneal injection of 250–300 ml of sterile physiological saline supplemented with oyster glycogen (2.5 mg/ml). At 16 h after injection, the inflammatory exudate was collected from the peritoneal cavity via a 16-gauge needle. The inflammatory AF was collected by sedimentation of the cells in the exudate by centrifugation at 100–200×g for 5 min; this was followed by centrifugation of the recovered supernatant at 20,000×g for 10 min to remove particulate material.

(2) Purfication of AF $PLA_2(II)$ $PLA_2(II)$ was purified from AF by chromatography on CM-Sephadex (Pharmacia), followed by a C4 reverse-phase HPLC column (1×25 cm, 5 $\mu$M particle size; Vydac, Hesperia, Calif.). AF was applied to CM-Sephadex that was preequilbrated in sterile physiological saline buffered with 10 mM Tris-HCl, pH 7.5, in a resin:AF volume ratio of 0.10. After washing the resin to remove unbound proteins, bound proteins were eluted with 1.5 M NaCl buffered with 20 mM sodium acetate/acetic acid (pH 4.0), and the eluates were dialyzed against 20 mM acetate buffer, pH 4.0.

Fractions containing bactericidal activity against *S. aureus* (see Example 2 below) were pooled (high salt eluate) and further purified by HPLC, using a first gradient of 0–95% acetonitrile in 0.1% trifluoroacetic acid developed over 30 min, followed by a gradient of 0–70% acetonitrile developed over 60 min. Eluted proteins were collected, dried, and resuspended in 20 mM acetate buffer before testing for antibacterial activity.

Recovery from the HPLC column of antibacterial activity against *S. aureus* was nearly 100%. Purity of the recovered fractions was analyzed by SDS-polyacrylamide gel electrophoresis on a Phast Gel system (Pharmacia) using Phast Gel 8–25% gradient polyacrylamide gels and Coomassie blue for detection of protein species and by $NH_2$-terminal amino acid sequence analysis and laser desorption mass spectral analysis. The protein content of fractions containing purified AF $PLA_2(II)$ was deduced from the measured catalytic activity and from the known specific catalytic activity of AF $PLA_2(II)$, and was confirmed by densitometric analysis of Coomassie blue-stained protein species following SDS-polyacrylamide gel electrophoresis using pig pancreas and human Group 11 $PLA_2(II)$s as standards.

EXAMPLE 2

Demonstration of Bactericidal Activity of Purified $PLA_2(II)$

A. Methods (1) Assay of bactercidal activity The effect of various protein fractions containing $PLA_2(II)$ on bacterial viability was determined by measuring the residual bacterial colony-forming ability of a culture after incubation with or without the protein fraction at 37° C. Typical incubation mixtures contained: a) $10^5$ bacteria in a total volume of 100 ml of 10 mM HEPES buffer (pH 7.4); b) the protein fraction being tested; and c) "AF filtrate" supplemented with 10 mg/ml of bovine serum albumin (to mimic the electrolyte and total protein content of the inflammatory fluid). AF filtrate was prepared by ultrafiltration of AF through a Centricon-10 membrane; Amicon Corp., Denvers, Mass., followed by sterile filtration. The resulting filtrate contained <0.3% of the total protein content of AF and no detectable antibacterial activity. Similar results were obtained using AF filtrate or Hanks' balanced salts solution (with divalent cations, HBSS+; BioWhittaker, Walkersville, Md.). Protein fractions in acetate buffer were added in a maximum of 10% of the total incubation volume.

To compare the antibacterial activities of plasma, serum and AP, incubations were carried out in buffered citrate. The antistaphylococcal activity of AF and serum was reduced by about 50% in mixtures containing buffered citrate as compared with those containing HEPES-buffered media.

To determine the effects of $Ca^{2+}$ and $Mg^{2+}$ on antistaphylococcal activity of purified $PLA_2(II)$, incubations were carried out in HBSS (without divalent cations) supplemented with divalent cations as indicated.

At the end of the incubation, aliquots of the suspensions were taken, serially diluted in sterile physiological saline and transferred to 5 ml of molten (480C) 1.3% (wt/vol) Bactoagar (Difco Laboratories, Inc., Detroit Mich.) containing 3% (wt/vol) trypticase soy broth (plus 0.5% horse blood for pneumococci and meningococci). Bacterial viability was measured as the number of colonies formed after incubation at 37° C. for 18–48 h.

(2) Anti-AF $PLA_2(II)$ serum Non-immune anti-AF $PLA_2(II)$ chicken sera were obtained as described in Wright et al, *J. Biol. Chem*, 265:6675 (1990) and were pretreated before use with liposorb (Calbiochem, La Jolla, Calif.) to deplete them of lipoproteins. The neutralizing effects of these antisera on the antistaphylococcal and $PLA_2(II)$ enzymatic activities of rabbit AF and serum were determined by preincubation of AF or serum with chicken serum for 30 min at room temperature in the standard incubation mixture prior to inclusion in either assay. Chicken serum itself contained no detectable antistaphylococcal or $PLA_2(II)$ enzymatic activity.

B. Results (1) Purification of Gram-positive bactericidal activity of AF yields 14 kDa $PLA_2(II)$ Fractionation by batch-wise adsorption of AF to CM-Sephadex and elution of bound proteins with 1.5 M NaCl (as described in Example 1 above) yielded potent anti-*S. aureus* activity in the high salt eluate. This fraction contains about 60% of the antibacterial activity of AF against *S. aureus* but less than 0.5% of the total AF protein. In contrast, proteins recovered in the unbound fraction, representing >95% of the total AF protein, exhibit little or no antistaphylococcal activity, either alone or in combination with the high salt eluate (FIG. 1).

Fractionation of the high salt eluate by reverse-phase HPLC on a C4 column gave a discrete peak of antistaphylococcal activity coincident with $PLA_2(II)$ enzymatic activity, each in nearly quantitative yield. By using shallower gradients of acetonitrile in 0.1% TFA, a fraction was obtained that contained a single protein species of 14 kDa (as judged by SDS-polyacrylamide gel electrophoresis) and both antistaphylococcal and $PLA_2(II)$ activities. Amino terminal amino acid sequence analysis confirmed that the protein was $PLA_2(II)$.

The antistaphylococcal activities of whole AF, the high salt eluate, and purified $PLA_2(II)$ were nearly identical when normalized to the $PLA_2(II)$ enzymatic activity of fractions (FIG. 1). This was true for each of five (clinical and laboratory) strains of *S. aureus* tested, including methicillin-resistant clinical isolates. The $LD_{90}$ of purified AF $PLA_2(II)$ toward these strains ($10^6$ bacteria/ml) ranged from 1,000–20,000 units (5–100 ng)/ml. At concentrations corresponding to those present in AF (about 200 ng/ml), and when tested under conditions that mimic the natural inflammatory fluid, purified $PLA_2(II)$ kills 2 logs of $10^7$ *S. aureus*/ml. Under these conditions, bacteria harvested in stationary phase were only slightly less sensitive than log phase bacteria to killing by either whole AF or purified AF $PLA_2(II)$.

Figure 2:
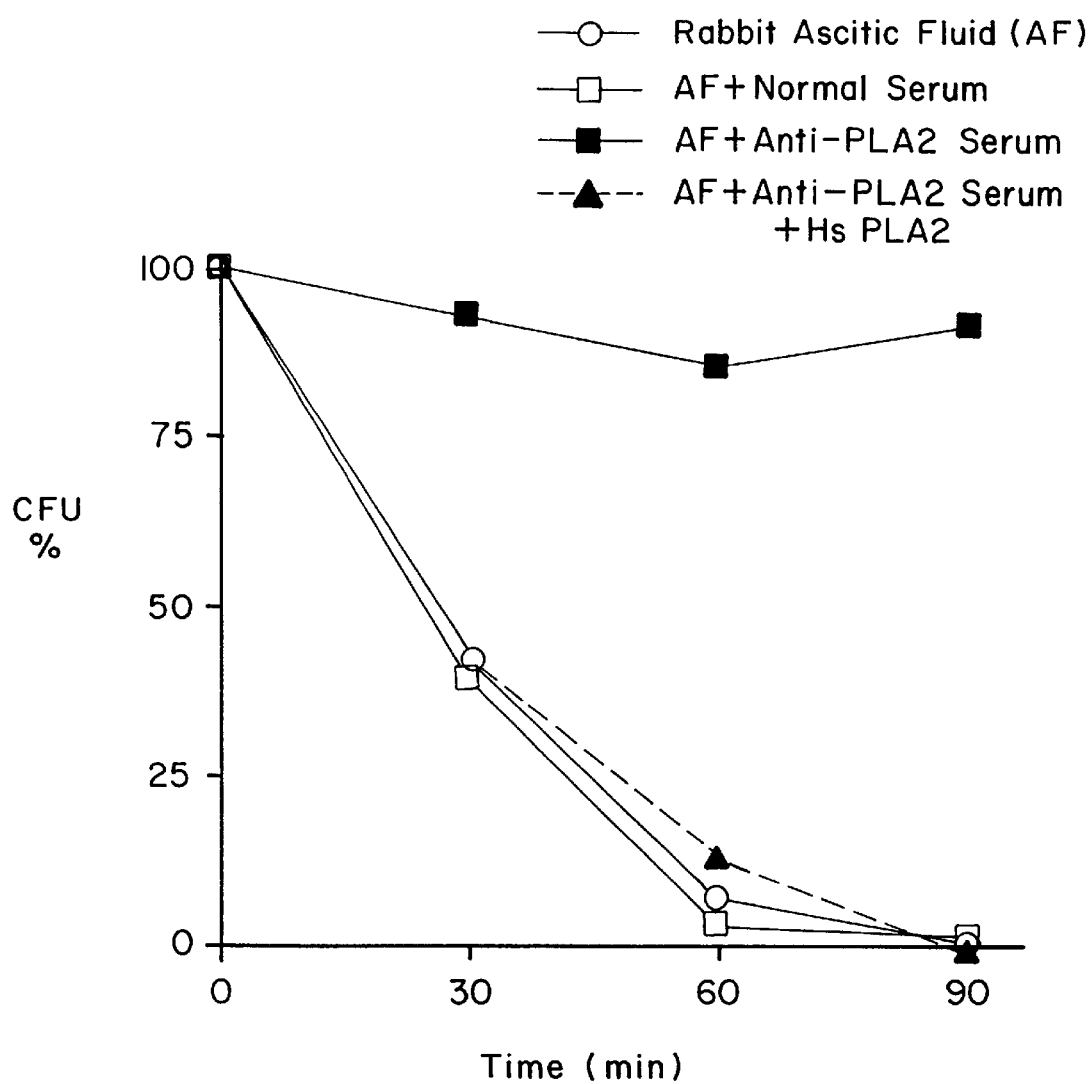
FIG. 2 is a graphic illustration of the effect of pre-incubation of rabbit ascitic fluid (AF) with anti-PLA$_2$(II) antiserum prior to measurement of its bactericidal effect against *S. aureus*.

(2) Antibacterial activity of AF against *S. aureus* is inhibited by anti-PLA$_2$(II) serum The remarkably similar antibacterial potency toward *S. aureus* of whole AF and purified PLA2(I) suggested that the activity of AF is due mainly to the action of PLA$_2$(II). In support of this hypothesis, killing of *S. aureus* by AF was blocked by pretreatment of AF with anti-PLA$_2$II but not normal chicken serum, using doses of immune serum that neutralized AF PLA$_2$(II) activity (FIG. 2). Moreover, addition of functionally similar but antigenically distinct recombinant human "secretory" PLA$_2$(II) fully restored the antistapbylococcal activity of AF pretreated with anti-PLA$_2$(II) serum (FIG. 2).

(3) Relationship of PLA2(II) to antistaphvlococcal activity in plasma and serum Serum also displays potent bactericidal activity toward *S. aureus*, whereas plasma collected from either unchallenged animals or from rabbits at the time of collection of AF possesses little or no anti-*S. aureus*, activity (Table 1).

TABLE 1

Comparison of antistaphylococcal and PLA$_2$(II) activities of Rabbit plasma and serum.

| Fraction | PLA$_2$(II) (Units/ml) | CFU (%)* |
|---|---|---|
| Plasma (0 hr)¥ | 4 ± 1.0 × 10$^3$ | 93 ± 11 |
| Plasma (16 hr)¥ | 5 ± 2.5 × 10$^3$ | 76 |
| Plasma (16 hr) + AF PLA$_2$(II) | 3 × 10$^4$ | 0 |
| Serum | 3 × 10$^4$ | 0 |
| Serum + anti-PLA$_2$(II) serumå | 3 × 10$^4$ | 155 |

*Effects of plasma and serum on viability of *S. aureus* (10$^6$ bacteria/ml) were measured as described in methods. Results are expressed as % of viability of bacteria incubated alone. The data shown represent the mean ± SEM of two or more determinations.
¥Plasma was collected just before (0 hr) or 16 h after intraperitoneal inoculation of glycogen/saline.
¶Serum was preincubated for 30 min at room temperature with 10% (vol/vol) normal (not shown) or anti-PLA2 chicken serum before assay of PLA2 and antistaphylococcal activities as described in Methods.

These differences in antistaphylococcal activity parallel differences in PLA$_2$(II) enzymatic activity, and the antibacterial activity against *S. aureus* of rabbit serum, like that of AF, is blocked by anti-PLA$_2$(II) chicken serum. Plasma supplemented with purified AF PLA$_2$(II) displays the same bactericidal activity toward *S. aureus* as serum and AF (Table 1). These findings indicate that PLA$_2$(II) accounts for the potent bactericidal activity against *S. aureus* of rabbit AF and serum that is normally absent in plasma.

EXAMPLE 3

Comparison of Antibacterial Activities of Various PLA$_2$(II) Polypeptides

The antibacterial activity of PLA$_2$(II) against *S. aureus* and *B. subtilis* was tested as described in Example 2 above, using PLA$_2$(II)s derived from different sources.

Human Group II PLA2 (HsPLA2) is the counterpart of the rabbit AF PLA$_2$(II) and also accumulates in inflammatory fluids (Weiss et al., *J.Biol. Chem.* 269:26331, 1994). The activity toward *S. aureus* of the recombinant human enzyme is closely similar to that of the rabbit AF PLA$_2$(II), whereas the PLA$_2$(II)s from pig pancreas, and both basic and acidic isozymes of *Naja mossambica mossambica* snake venom, are inactive even at doses 10,000 times the LD$_{90}$ of AF PLA$_2$(II) (Table 2).

*B. subtilis* is 50-fold more sensitive than *S. aureus* to rabbit and human inflammatory fluid PLA$_2$(II) (LD$_{90}$= 10–50 pM), but is also resistant to the other enzymes even at 100 to 1000-fold higher concentrations.

BPI-treated *E. coli* cells are also sensitive to the inflammatory fluid PLA$_2$(II)s and resistant to the pancreatic and acidic venom PLA$_2$(II)s, but are highly sensitive to the basic venom enzyme. This indicates that the structural determinants of PLA$_2$(II) activity toward Gram-positive and BPI-treated Gram-negative bacteria overlap in part but are not identical.

This conclusion is supported by the effects of site-specific mutations (R7S.K15Q) on the antibacterial activity of the human PLA$_2$(II) that markedly reduce enzyme activity toward BPI-treated *E. coli* but have less pronounced effects on bactericidal activity against *S. aureus* and *B. subtilis*. Further, a site-specific substitution of pig pancreas PLA$_2$(II) (S7R(K)) that results in an active enzyme toward BPI-treated *E. coli* does not elicit antibacterial activity toward *S. aureus* or *B. subtilis* (Table 2).

TABLE

Comparison of antibacterial activities of various 14 kDa Pla$_2$(II)s

| PLA 2 | *S. aureus* L D$_{90}$ (ng/mL) | *S. aureus* L D$_{90}$ (ng/mL) | BPI-treated *E. coli* (ng/10$^7$ bacteria)$^£$ |
|---|---|---|---|
| Rabbit AF (II)§ | 10 | 0.2 | 2 |
| Human secretory (II | | | |
| Wild type | 50 | | |
| | | 0.8 | 2 |
| Wild type: p-BPB† treated | Not Active (500)* | | |
| | | N.T.¥ | Not Active (50) |
| R7S.K15Q | 700 | | |
| | | 1.25 | 50 |
| Pig Pancreas (I) | | | |
| Wild type | Not Active (20,000) | Not Active (10,000) | Not Active (10000) |
| S7R(K) | Not Active (40,000) | Not Active (10,000) | 100 |

TABLE-continued

Comparison of antibacterial activities of various 14 kDa Pla$_2$(II)s

| PLA 2 | S. aureus L D$_{90}$ (ng/mL) | S. aureus L D$_{90}$ (ng/mL) | BPI-treated E. coli (ng/10$^7$ bacteria)$^£$ |
|---|---|---|---|
| *Naja mossambica mossambica* (I) | | | |
| CMI (acidic) | Not Active (80,000) | Not Active (10,000) | Not Active (1000) |
| CMIII (basic) | Not Active (100,000) | 250 | 25 |

£PLA$_2$(II) dose required to produce degradation of ≧10 % of phospholipids of BPI-treated *E. coli*.
§Number in parentheses refers to group of 14 kDa PLA$_2$(II)
†p-bromophenacylbromide
*Highest Dose Tested
¥N.T. Not Tested

EXAMPLE 4

Antistaphylococcal Activity of PLA$_2$(II) Depends on Catalytic Activity and Ca$^{2+}$ The experiments described below were performed to evaluate the relationship between the enzymatic and antibacterial activities of PLA$_2$(II). For this purpose, covalent modification of the active site histidine of Hs-PLA$_2$(II) was achieved by treatment with p-bromophenacylbromide, and the enzymatic and antibacterial activities were tested as described in Example 2 above. This treatment inactivated both enzymatic and antistaphylococcal activities (see Table 2 above).

The calcium dependence of PLA$_2$(II)-mediated bacterial killing was also measured. *S. aureus* (1×10$^5$ bacteria/ml) were incubated at 37° C. with 80 ng/ml of AF PLA2(II) in 10 mM HEPES-buffered HBSS (without divalent cations) to which divalent cations were added as indicated. After 90 min, bacterial viability was measured as described in Example 2 above. The results (shown in Table 3 below) are expressed as percent of colony-forming units observed in cultures containing added divalent cations relative to controls.

TABLE 3

| Divalent citations added | CFU (%) |
|---|---|
| None | 68 |
| 1 mM Ca$^{2+}$ | 6 |
| 1 mM M$^{2+}$ | 92 |
| 20 mM Ca$^{2+}$ | 85 |
| 1 mM Ca$^{2+}$ + 20 mM Mg$^{2+}$ | 122 |

The bactericidal action of both AF and (Hs) PLA$_2$(II) against *S. aureus* is Ca$^{2+}$-dependent. Half-maximal activity required about 20 µM Ca$^{2+}$, and full activity was expressed at Ca$^{2+}$ concentrations ranging from 0.1–2 mM. Mg$^{2+}$ does not support the bactericidal activity of PLA$_2$(II). Furthermore, at supraphysiological concentrations (20 mM), both Ca$^{2+}$ and Mg$^{2+}$ inhibit the antistaphylococcal activity of PLA$_2$(II).

EXAMPLE 5

Antibacterial Action of PLA$_2$(II) is Accompanied by Bacterial Phospholipid Degradation and Other Structural Alterations The experiments described below were performed to evaluate whether or not degradation of bacterial phospholipids is required for bactericidal activity of PLA$_2$(II).

A. Methods (1) Radiolabeling of lipids of *S. aureus* during growth To uniformly label the lipids (mainly phosphatidylglycerol, PG) of *S. aureus* to high specific radioactivity, the bacteria were grown in subculture at 37° C. in nutrient broth supplemented with 2.5 µCi/ml of [1-$^{14}$C] oleic acid (56 mCi/mmol; DuPont-New England Nuclear). Bacteria were grown to mid-log phase, washed, resuspended in fresh media without oleic acid, incubated at 37° C. for 20–30 min, and, finally, washed in media supplemented with 0.5% albumin (wt/vol).

(2) Extaction and chromatographic anatlsis of radiolabelled bacterial lipids To identify the bacterial molecular species labelled with [1-$^{14}$C] oleic acid, labelled bacteria were extracted according to the procedure of Bligh & Dyer (*Can.J.Physiol.* 37:911, 1959), and the extracted labelled species were resolved by thin-layer chromatography (TLC) on silica gel G (Analtech, Newark, Del.) and quantified by liquid scintillation counting. To facilitate identification of the labelled species, samples were supplemented with unlabelled lipids [?] after TLC to detect the lipid standards.

Greater than 95% of the incorporated radioactivity was recovered in the CHCl$_3$ phase, approximately 90% of which remained at the origin along with PG during TLC in petroleum ether/diethyl ether/glacial acetic acid (80:20:1;vol/vol/vol), while 10% comigrated with diglyceride and <2% comigrated with free fatty acid.

The species at the origin were eluted with CHCl$_3$/CH$_3$OH/acetic acid/water (50/30/8/4) and resolved by TLC in CHCl$_3$/CH$_3$OH/water/acetic acid (65/25/4/1), revealing that about 80% of these labelled species comigrated with PG. The identity of these species as PG was confirmed by elution and TLC in CHCl$_3$/CH$_3$OH/acetic acid (7/3/1) and CHCl$_3$/CH$_3$OH/30% ammonium hydroxide (65/35/5).

To determine the acyl chain position of [1-$^{14}$C] oleic acid incorporated into PG, eluted radiolabelled PG was dried, resuspended in physiological saline containing 10 mM CaCl$_2$, 50 mM Tris-HCl (pH 7.5) and 1 mg/ml albumin, sonicated for 10 min at 40° C. in a water bath sonicator (40 W) to disperse the phospholipid (1–2 mnol/100 µl) and incubated for 60 min with 50 ng/ml of AF PLA$_2$(II). After the incubation, labelled lipids and products were extracted and resolved by TLC as described above. Nearly quantitative degradation by the added PLA$_2$(II) of labelled PG was accompanied by a reciprocal accumulation of labeled lyso-PG distributed between the CHCl$_3$ and H$_2$O/CH$_3$OH phases after Bligh/Dyer extraction. There was little or no accumulation of labelled free fatty acid (<5% of the total labelled product formed). Thus, [1-$^{14}$C] oleic acid was incorporated almost exclusively into the 1-acyl position of PG consistent with previous studies of acyl chain distribution in *S. aureus* lipids.

(3) Measurement of bacterial phospholipid (PG) degradation during treatment of Saureus with purified PLA$_2$(II) [1-$^{14}$C] oleate-prelabelled *S. aureus* (2500 cpm/10$^6$ bacteria) were incubated with or without PLA$_2$(II) in the standard incubation mixture, except that 5×10$^6$ bacteria/ml were used. After the incubation, samples were extracted and resolved by TLC as described above. Radiolabelled species recovered in the H$_2$O/CH$_3$OH phase (e.g. lyso-PG) were dried, resuspended in CH$_3$OH and resolved by TLC. The identity of the degraded lipid species and accumulating product(s) was determined by TLC in each of the solvent systems described above.

(4) Radiolabeling of proteins to *S. aureus* during growth
To label the proteins of *S. aureus* to high specific radioactivity, the bacteria were grown at 37° C. in methionine assay medium (Difco) supplemented with 3–5 μCi/ml of $^{35}$S-methionine (1175 Ci/mmol; DuPont-New England Nuclear) and 600 ng/ml of unlabelled methionine. The bacteria were grown to mid-log phase, washed once, resuspended in fresh medium with unlabelled methionine and incubated an additional 20–30 min at 37° C. before harvesting. The labelled bacteria contained 3000 cpm/10$^6$ bacteria, >90% of which were precipitable in 10% trichloroacetic acid.

(5) Measurement of bacterial protein release $^{35}$S-methionine-prelabelled *S. aureus* were incubated with or without PLA$_2$(II) in the standard incubation mixture, except that 10$^7$ bacteria/ml were used. After the incubation, the bacteria were sedimented at 14,000×g for 5 min, and the radioactivity in an aliquot of the recovered supernatant was measured both directly and after precipitation with 10% trichloroacetic acid to monitor release and degradation of labelled bacterial proteins.

B. Results

Figure 3A:
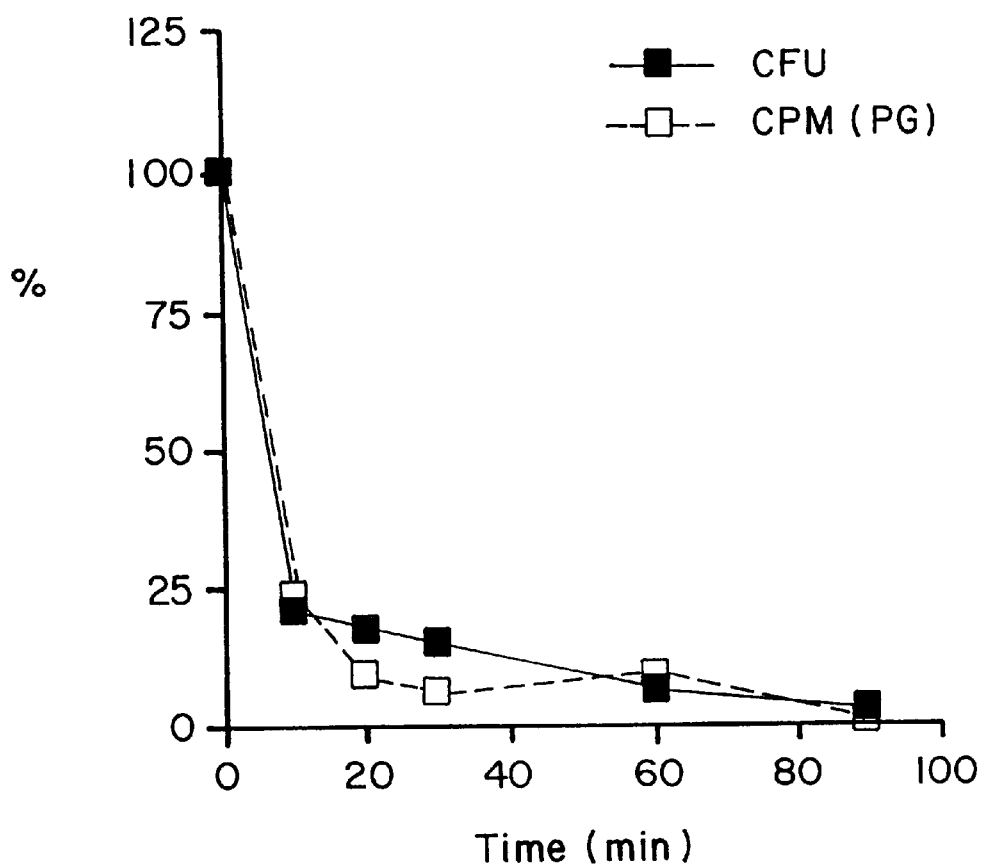
FIG. 3 is a graphic illustration of the degradation of bacterial hosphatidylglycerol (PG) (left panel) and release of bacterial proteins (right panel) during reatment of *S. aureus* with purified AF PlA$_2$(II).
Figure 3B:
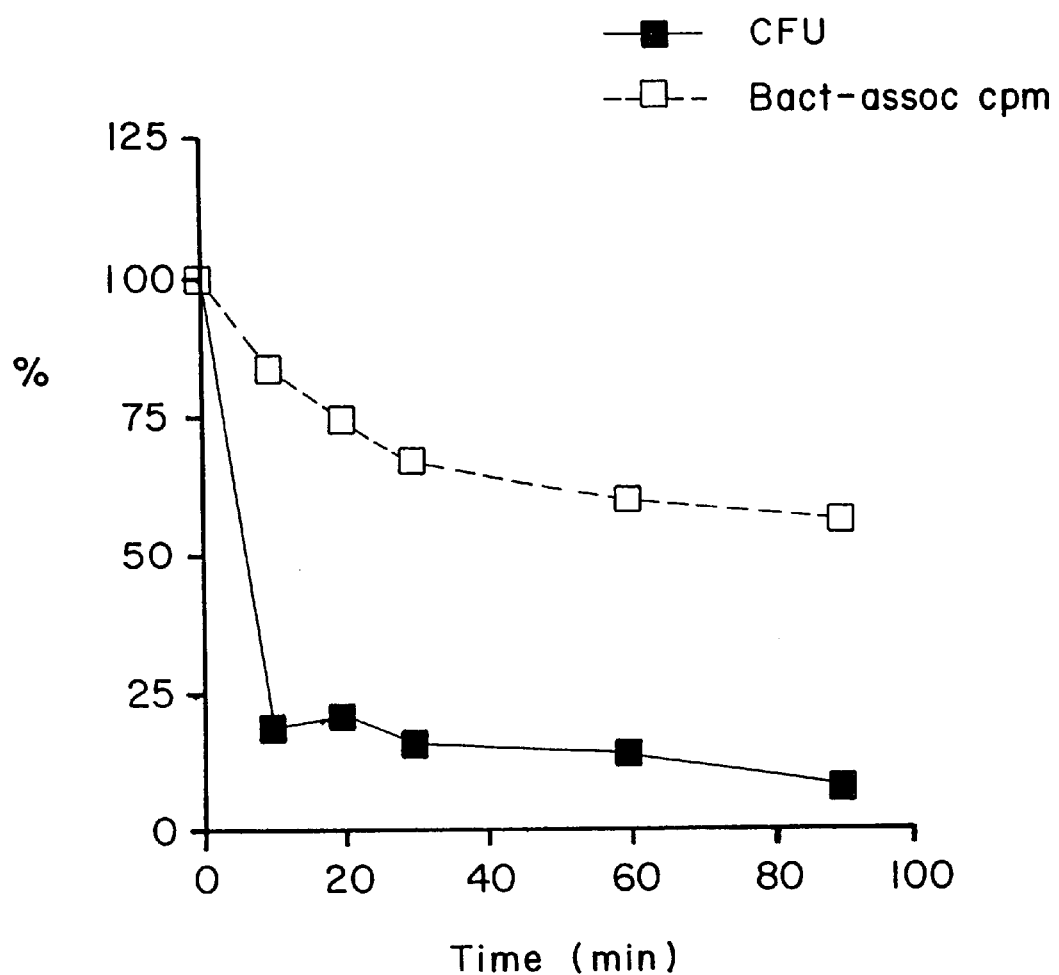

To measure phospholipid degradation, *S. aureus* lipids were prelabelled during growth with radioactive fatty acids. As judged by chromatographic and iochemical analyses (see above), >65% of the labelled lipids were phosphatidylglycerol (PG; the predominant phospholipid species in *S. aureus*) and >90% of the radiolabel was in the 1-acyl position. Treatment of *S. aureus* with a lethal dose of PLA2(II) produced, in parallel to bacterial killing, nearly quantitative degradation of PG (FIG. 3, left panel), and, to a lesser extent, cardiolipin, as well as to accumulation of labelled lyso-PG, consistent with the acyl position specificity of the added PLA$_2$(II). Little or no degradation was produced by "inactive" (e.g., pig pancreas) PLA$_2$(II).

The enormous amount of bacterial envelope phospholipid degradation produced by lethal doses of PLA$_2$(II) suggested that this treatment could cause extensive overall envelope disruption. Bacterial killing by PLA$_2$(II) was accompanied by the release of about 50% of TCA-precipitable $^{35}$S-methionine-labelled bacterial material and the loss of Gram-positive staining (FIG. 3, right panel) indicative of substantial damage to the integrity of both the cell wall and the cytoplasmic membrane.

EXAMPLE 6

Comparison of the Bactericidal Activity of Unfractionated AF and Purified AF PLA$_2$(II) Against Different Bacterial Species The experiments described below were performed to compare the antibacterial activity of PIA$_2$(II) against different bacterial species. These assays were performed essentially as described in Example 2 above. Bacteria (10$^6$/ml) were incubated for 120 minutes in 90% (vol/vol) ascitic fluid buffered with 10 mM HEPES, pH 7.4 or in HEPES buffered ascitic fluid filtrate with or without 30,000 units/ml of purified ascitic fluid PLA$_2$(II).

The results are illustrated in Table 4 below.

TABLE 4

| ORGANISM | BACTERICIDAL ACTIVITY | |
| --- | --- | --- |
| | Unfractionated AF | Purified PLA$_2$(II) |
| A. Gram-Positive | | |
| *Staphylococcus aureus* | | |
| *Staphylococcus saprophyticus* | +++ | +++ |
| *Streptococcus pneumoniae* (nonencapsulated) | +++ | ++ |
| *Streptococcus salivarius* | +++ | + |
| *Staphylococcus epidermidis* | ++ | ++ |
| *Steptococcus pyogenes* | ++ | ++ |
| *Enterococcus faecalis* | + | + |
| *Streptococcus pneumoniae* (Type III Capsule) | − | − |
| B. Gram Negative Bacteria | | |
| *Escherichia coli* | +++ | − |
| *Neisseria meningitidis* | +++ | − |
| *Shigella sonnei* | +++ | − |

+++ Less than 10% survival
++ 10% to 30% survival
+ 30% to 60% survival
− no effect Both unfractionated AF and purified AF PLA$_2$(II) displayed potent bactericidal activity against several different species of Staphylococci and Streptococci, including Group A *S. pyogenes*. The effects of AF and a corresponding amount of purified PLA$_2$(II) against several Gram-positive bacterial species were closely similar. In contrast, the activity of whole AF toward *S. salivarius* exceeded that of purified PLA$_2$(II), implying that other factor(s) in AF contribute to killing this organism. Similarly, toward each of the Gram-negative bacteria tested, purified AF PLA$_2$(II) exhibited no antibacterial activity, whereas whole AF possessed potent bactericidal activity. Notably, the presence of a type III capsule in *S. pneumoniae* rendered this organism resistant to the effects of purified PLA$_2$(II) and unfractionated AF.

EXAMPLE 7

Killing of Antibiotic-resistant Strains of *Staphylococcus aureus* by PLA$_2$(II)

Figure 4:
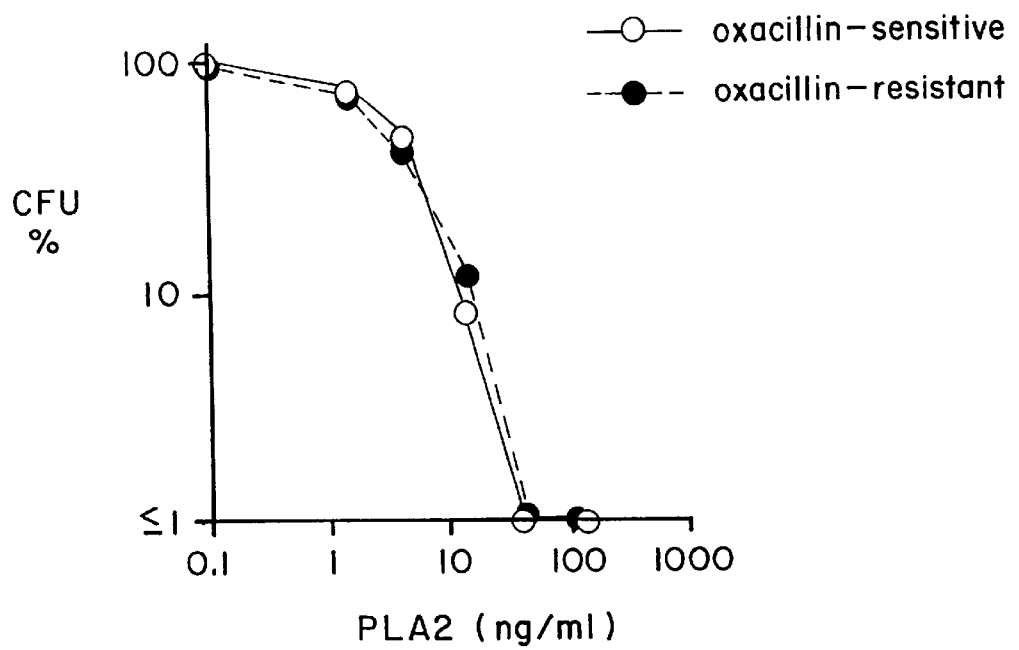
FIG. 4 is a graphic illustration of the dose-dependent antibacterial effects of purified rabbit AF PLA$_2$(II) on oxacillin-sensitive and oxacillin-resistant strains of *S. aureus*.

The bactericidal activity of PLA$_2$(II) against antibiotic-resistant strains of *S. aureus* was measured as described in Examples 2 and 6 above. As can be seen in FIG. 4, AF PLA$_2$(II) shows equal bactericidal potency against oxacilin (methicillin)-sensitive and oxacillin-resistant strains of *S. aureus*.

EXAMPLE 8

Enhancement of Gram-positive Bactericidal Activity of PLA2(II) by Human Serum

The experiments described below were performed to test the bactericidal activity of PLA2(II) under clinically significant conditions. Incubation mixtures containing 10$^5$ *S. aureus* cells and increasing amounts of PLA2(II) (as described in Example 2 above) were prepared in the absence and presence of human serum buffered with 10 mM Hepes pH 7.4; control mixtures contained buffer alone in place of serum. After incubation at 37° C., the number of viable bacterial cells was determined as described in Example 2 above.

Figure 5:
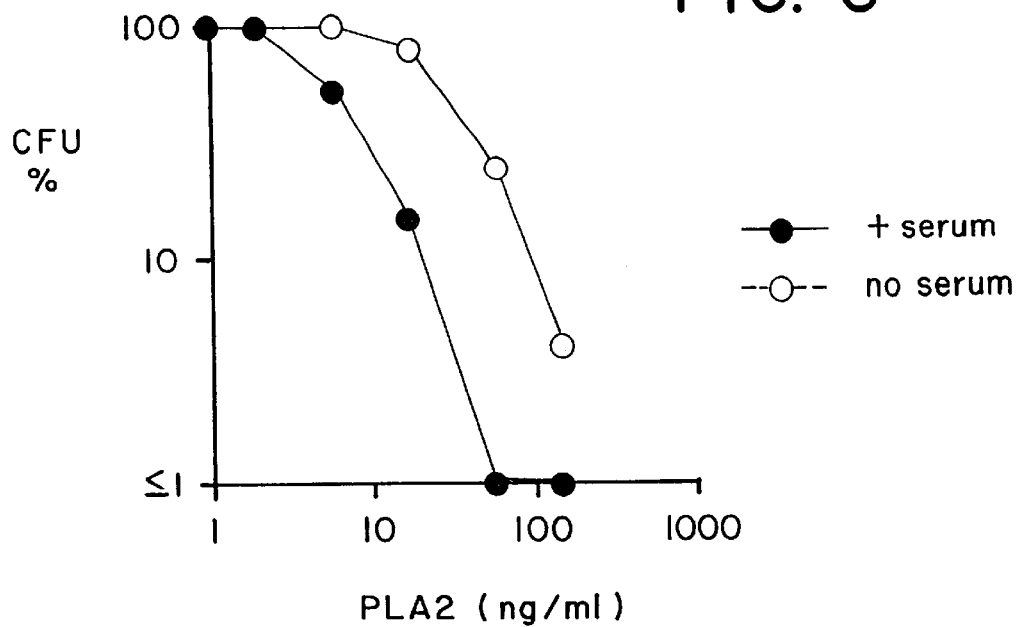
FIG. 5 is a graphic illustration of the bactericidal effects of PLA$_2$(II) on *S. aureus* in the absence and presence of human serum.

As shown in FIG. 5, the bactericidal activity of $PLA_2(II)$ is considerably enhanced (at least 5-fold) in the presence of human serum. This demonstrates that PLA2(II) is clinically applicable to the treatment of bacteremias in humans. Furthermore, the dosage of $PLA_2(II)$ required to achieve clinical benefit is likely to be even lower than estimated from in vitro assays.

EXAMPLE 9

Mobilization of Gram-Postive Bactericidal Activity During Systemic Bacterial Challenge As shown above, extracellular mobilization of Group II 14 kD PLA2 in glycogen-induced rabbit inflammatory peritoneal exudates is responsible for the potent bactericidal activity of the inflammatory fluid toward *Staphylococcus aureus* and other Gram-positive bacteria. Because similar levels of PLA2 are induced in plasma during systemic inflammation, the question of whether this gives rise to plasma bactericidal activity not present in resting animals was tested as set forth below.

Baboons were injected i.v. with a lethal dose of *E. coli* ($10^{11}$ bacteria/kg body weight) and sera collected before and at hourly intervals after injection. Before infusion of bacteria, serum did not kill *S. aureus* ($10^6$/ml) and contained >2000 U PLA2/ml. PLA2 levels and, in parallel, antistaphylococcal activity increased approximately 100-fold over 24 h. Serun collected at 24 h killed >99.9% of $10^6$ *S. aureus*/ml; this activity was completely blocked by a monoclonal antibody to human Group II PLA2. Addition of recombinant human PLA2 to pre-challenge serum brought the anfistaphylococcal activity to the level of the 24 h post-challenge serum. PLA2-dependent bactericidal activity was enhanced approximately 10-fold by factor(s) present constitutively in plasma/serum.

These findings further demonstrate the contribution of Group II PLA2 to the bactericidal potency of biological fluids and suggest that mobilization of this enzyme during inflammation may play an important role in host defense against invading Gram-positive bacteria.

What is claimed is:

1. A pharmaceutical formulation comprising
    a mammalian Type II phospholipase A2, a pharmaceutically acceptable carrier or diluent, and a member selected from the group consisting of excipients preservatives and stabilizers.
2. The formulation of claim 1, wherein said mammalian species is selected from the group consisting of human, cow, rabbit, rat, mouse, cat, and dog.
3. The formulation of claim 1 further comprising a β-lactam antibiotic.
4. A dosage unit for treating a mammal suffering from an infection caused by a Gram-positive bacteria comprising
    a mammalian Type II phospholipase A2;
    an excipient; and
    a physiologically acceptable carrier or diluent.
5. The dosage unit of claim 4 wherein said excipient is selected from the group consisting of lubricants, plasticizers, colorants, absorption enhancers and bacteriacides.
6. The dosage unit of claim 4 wherein said dosage unit is selected from the group consisting of a liquid, a capsule, a tablet, a suppository and a powder.
7. A pharmaceutical formulation comprising
    a mammalian Type II phospholipase A2;
    a β-lactam antibotic and a pharmaceutically acceptable carrier or diluent.

* * * * *